United States Patent
Wright et al.

(10) Patent No.: US 6,726,699 B1
(45) Date of Patent: Apr. 27, 2004

(54) INSTRUMENT GUIDE

(75) Inventors: James Wright, Santa Barbara, CA (US); Jim Deacon, Goleta, CA (US); Hendrik S. Westra, Goleta, CA (US)

(73) Assignee: Computer Motion, Inc., Sunnyvale, CA (US)

( * ) Notice: Subject to any disclaimer, the term of this patent is extended or adjusted under 35 U.S.C. 154(b) by 0 days.

(21) Appl. No.: 09/639,489

(22) Filed: Aug. 15, 2000

(51) Int. Cl.[7] .............................................. A61B 17/34
(52) U.S. Cl. ...................................................... 606/185
(58) Field of Search ............................ 606/1, 108, 184, 606/185, 170, 190; 604/164.01, 264

(56) References Cited

U.S. PATENT DOCUMENTS

| | | |
|---|---|---|
| 977,825 A | 12/1910 | Murphy |
| 3,171,549 A | 3/1965 | Orloff |
| 3,280,991 A | 10/1966 | Melton et al. |
| 4,058,001 A | 11/1977 | Waxman |
| 4,128,880 A | 12/1978 | Cray, Jr. |
| 4,221,997 A | 9/1980 | Flemming |
| 4,367,998 A | 1/1983 | Causer |
| 4,401,852 A | 8/1983 | Noso et al. |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,641,292 A | 2/1987 | Tunnell et al. |

(List continued on next page.)

FOREIGN PATENT DOCUMENTS

| | | |
|---|---|---|
| DE | U 9204118.3 | 7/1992 |
| DE | 4310842 C2 | 1/1995 |
| EP | 0239409 A1 | 9/1987 |
| EP | 0424687 A1 | 5/1991 |

(List continued on next page.)

OTHER PUBLICATIONS

"Endocorporeal Surgery Using Remote Manipulators" (Ned S. Rasor and J.W. Spickler) Remotely Manned Systems—Exploration and Operation in Space, California Institute of Technology 1973.

"A Survey Study of Teleoperators, Robotics, and Remote Systems Technology" (Arthur D. Alexander, III) Remotely Manned Systems—Exploration and Operation in Space, California Institute of Technology 1973.

(List continued on next page.)

*Primary Examiner*—Max F. Hindenburg
*Assistant Examiner*—Brian Szmal
(74) *Attorney, Agent, or Firm*—Townsend & Townsend & Crew LLP

(57) ABSTRACT

An instrument guide that can compensate for surgical instruments that have different outer diameters. The instrument guide includes a shaft that has an inner channel adapted to receive a surgical instrument. The guide also has a leaf that can be deflected relative to the shaft to exert a spring force onto the instrument. The amount of leaf deflection is dependent upon the outer diameter of the surgical instrument.

10 Claims, 2 Drawing Sheets

U.S. PATENT DOCUMENTS

| | | |
|---|---|---|
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,815,006 A | 3/1989 | Anderson et al. |
| 4,815,450 A | 3/1989 | Patel |
| 4,837,734 A | 6/1989 | Ichikawa et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,979,933 A | 12/1990 | Runge |
| 4,979,949 A | 12/1990 | Matsen, III et al. |
| 4,980,626 A | 12/1990 | Hess et al. |
| 4,989,253 A | 1/1991 | Liang et al. |
| 4,996,975 A | 3/1991 | Nakamura |
| 5,019,968 A | 5/1991 | Wang et al. |
| 5,020,001 A | 5/1991 | Yamamoto et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,105,367 A | 4/1992 | Tsuchihashi et al. |
| 5,109,499 A | 4/1992 | Inagami et al. |
| 5,123,095 A | 6/1992 | Papadopulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,187,574 A | 2/1993 | Kosemura et al. |
| 5,196,688 A | 3/1993 | Hesse et al. |
| 5,201,325 A | 4/1993 | McEwen et al. |
| 5,201,743 A | 4/1993 | Haber et al. |
| 5,217,003 A | 6/1993 | Wilk |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,251,127 A | 10/1993 | Raab |
| 5,257,999 A | 11/1993 | Slanetz, Jr. |
| 5,271,384 A | 12/1993 | McEwen et al. |
| 5,279,309 A | 1/1994 | Taylor et al. |
| 5,282,806 A | 2/1994 | Haber |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |
| 5,417,210 A | 5/1995 | Funda et al. |
| 5,417,701 A | 5/1995 | Holmes |
| 5,422,521 A | 6/1995 | Neer et al. |
| 5,431,645 A | 7/1995 | Smith et al. |
| 5,434,457 A | 7/1995 | Josephs et al. |
| 5,442,728 A | 8/1995 | Kaufman et al. |
| 5,443,484 A * | 8/1995 | Kirsch et al. ............... 606/185 |
| 5,445,166 A | 8/1995 | Taylor |
| 5,451,924 A | 9/1995 | Massimino et al. |
| 5,455,766 A | 10/1995 | Scheller et al. |
| 5,458,547 A | 10/1995 | Teraoka et al. |
| 5,458,574 A | 10/1995 | Machold et al. |
| 5,476,010 A | 12/1995 | Fleming et al. |
| 5,490,117 A | 2/1996 | Oda et al. |
| 5,490,843 A * | 2/1996 | Hildwein et al. ...... 606/164.01 |
| 5,506,912 A | 4/1996 | Nagasaki et al. |
| 5,512,919 A | 4/1996 | Araki |
| 5,515,478 A | 5/1996 | Wang |
| 5,544,654 A | 8/1996 | Murphy et al. |
| 5,553,198 A | 9/1996 | Wang et al. |
| 5,562,503 A | 10/1996 | Ellman et al. |
| 5,571,110 A | 11/1996 | Matsen, III et al. |
| 5,572,999 A | 11/1996 | Funda et al. |
| 5,609,560 A | 3/1997 | Ichikawa et al. |
| 5,620,456 A * | 4/1997 | Sauer et al. ........... 604/164.01 |
| 5,626,595 A | 5/1997 | Sklar et al. |
| 5,629,594 A | 5/1997 | Jacobus et al. |
| 5,630,431 A | 5/1997 | Taylor |
| 5,631,973 A | 5/1997 | Green |
| 5,636,259 A | 6/1997 | Khutoryansky et al. |
| 5,649,956 A | 7/1997 | Jensen et al. |
| 5,657,429 A | 8/1997 | Wang et al. |
| 5,658,250 A | 8/1997 | Blomquist et al. |
| 5,676,673 A | 10/1997 | Ferre et al. |
| 5,695,500 A | 12/1997 | Taylor et al. |
| 5,696,574 A | 12/1997 | Schwaegerle |
| 5,696,837 A | 12/1997 | Green |
| 5,704,900 A | 1/1998 | Dobrovolny et al. |
| 5,718,038 A | 2/1998 | Takiar et al. |
| 5,727,569 A | 3/1998 | Benetti et al. |
| 5,735,290 A | 4/1998 | Sterman et al. |
| 5,737,711 A | 4/1998 | Abe |
| 5,749,362 A | 5/1998 | Funda et al. |
| 5,754,741 A | 5/1998 | Wang et al. |
| 5,762,458 A | 6/1998 | Wang et al. |
| 5,766,126 A | 6/1998 | Anderson |
| 5,776,126 A | 7/1998 | Wilk et al. |
| 5,779,623 A | 7/1998 | Bonnell |
| 5,792,135 A | 8/1998 | Madhani et al. |
| 5,792,178 A | 8/1998 | Welch et al. |
| 5,797,900 A | 8/1998 | Madhani et al. |

| | | |
|---|---|---|
| 5,800,423 A | 9/1998 | Jensen |
| 5,807,284 A | 9/1998 | Foxlin |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,813,813 A | 9/1998 | Daum et al. |
| 5,814,038 A | 9/1998 | Jensen et al. |
| 5,817,084 A | 10/1998 | Jensen |
| 5,825,982 A | 10/1998 | Wright et al. |
| 5,827,319 A * | 10/1998 | Carlson et al. ............. 604/264 |
| 5,836,869 A | 11/1998 | Kudo et al. |
| 5,844,824 A | 12/1998 | Newman et al. |
| 5,855,583 A | 1/1999 | Wang et al. |
| 5,859,934 A | 1/1999 | Green |
| 5,860,995 A | 1/1999 | Berkelaar |
| 5,876,325 A | 3/1999 | Mizuno et al. |
| 5,878,193 A | 3/1999 | Wang et al. |
| 5,882,206 A | 3/1999 | Gillio |
| 5,887,121 A | 3/1999 | Funda et al. |
| 5,888,190 A | 3/1999 | Meyer et al. |
| 5,904,702 A | 5/1999 | Ek et al. |
| 5,906,630 A | 5/1999 | Anderhub et al. |
| 5,931,832 A | 8/1999 | Jensen |
| 5,950,629 A | 9/1999 | Taylor et al. |
| 5,951,475 A | 9/1999 | Gueziec et al. |
| 5,951,587 A | 9/1999 | Qureshi et al. |
| 5,954,731 A | 9/1999 | Yoon |
| 5,957,902 A * | 9/1999 | Teves ........................ 606/185 |
| 5,980,782 A | 11/1999 | Hershkowitz et al. |
| 5,984,932 A | 11/1999 | Yoon |
| 6,024,695 A | 2/2000 | Taylor et al. |
| 6,036,641 A | 3/2000 | Taylor et al. |
| 6,102,854 A | 8/2000 | Cartier et al. |
| 6,113,534 A | 9/2000 | Koros et al. |
| 6,120,433 A | 9/2000 | Mizuno et al. |
| 6,290,644 B1 | 9/2001 | Green, II et al. |
| 6,306,146 B1 | 10/2001 | Dinkler |
| 6,315,718 B1 | 11/2001 | Sharratt |
| 6,331,157 B2 | 12/2001 | Hancock |
| 6,371,906 B1 | 4/2002 | Borst et al. |
| 6,432,121 B1 * | 8/2002 | Jervis ........................ 606/190 |
| 2002/0014567 A1 | 2/2002 | King et al. |
| 2002/0045888 A1 | 4/2002 | Ramans et al. |
| EP | 0776738 A2 | 6/1997 |
| WO | WO 91/04711 | 4/1991 |
| WO | WO 92/20295 | 11/1992 |
| WO | WO 93/13916 | 7/1993 |
| WO | WO 94/18881 | 9/1994 |
| WO | WO 94/26167 | 11/1994 |
| WO | WO 97/15240 | 5/1997 |
| WO | WO 98/25666 | 6/1998 |

OTHER PUBLICATIONS

"Impacts of Telemation on Modern Society" (Arthur D. Alexander, III), On the Theory and Practice of Robots and Manipulators vol. II, 1974.

Transcript of a video presented by SRI at the 3rd World Congress of Endoscopic Surgery in Bordeaux on Jun. 18–20, 1992, in Washington on Apr. 9, 1992, and in San Diego, CA on Jun. 4–7, 1992 entitled "Telepresence Surgery—The Future of Minimally Invasive Medicine".

Statutory Declaration of Dr. Philip S. Green, presenter of the video entitled "Telepresence Surgery—The Future of Minimally Invasive Medicine".

Abstract of a presentation "Telepresence: Advanced Teleoperator Technology for Minimally Invasive Surgery" (P. Green et al.) given at the 3rd World Congress of Endoscopic Surgery in Bordeaux, Jun. 18–20, 1992.

Abstract of a presentation "Telepresence: Advanced Teleoperator Technology for Minimally Invasive Surgery", (P. Green et al.) given at "Medicine meets virtual reality" symposium in San Diego, Jun. 4–7, 1992.

Abstract of a presentation "Camera Control for Laparoscopic Surgery by Speech–Recognizing Robot: Constant Attention and Better Use of Personnel" (Colin Besant et al.) given at the 3rd World Congress of Endoscopic Surgery in Bordeaux, Jun. 18–20, 1992.

"A Literature Review: Robots in Medicine" (B. Preising et al.) IEEE Jun. 1991.

"Robots for the Operating Room" (Elizabeth Corcoran), The New York Times, Sunday Jul. 19, 1992, Section 3, p. 9, Col. 1.

"Taming the Bull: Safety in a Precise Surgical Robot" (Russell H. Taylor et al.), IEEE 1991.

Abstract of a presentation "Design Considerations of a New Generation Endoscope Using Robotics and Computer Vision Technology" (S.M. Krishnan et al.) given at the 3rd World Congress of Endoscopic Surgery in Bordeaux, Jun. 18–20, 1992.

Abstract of a presentation "3–D Vision Technology Applied to Advanced Minimally Invasive Surgery Systems" given at the 3rd World Congress of Endoscopic Surgery in Bordeaux, Jun. 18–20, 1992.

"Analysis of the Surgeon's Grasp for Telerobotic Surgical Manipulation" (Frank Tendick and Lawrence Stark), IEEE 1989.

"Kinematic Control and Visual Display of Redundant Teleoperators" (Hardi Das et al.), IEEE 1989.

"A New System for Computer Assisted Neurosurgery" (S. Lavallee), IEEE 1989.

"An Advanced Control Micromanipulator for Surgical Applications" (Ben Gayed et al.), Systems Science vol. 13 1987.

"Force Feedback–Based Telemicromanipulation for Robot Surgery on Soft Tissues" (A.M. Sabatini et al.), IEEE 1989.

"Six–Axis Bilateral Control of an Articulated Slave Manipulator Using a Cartesian Master Manipulator" (Masao Inoue), Advanced Robotics 1990.

"On a Micro–Manipulator for Medical Application—Stability Consideration of its Bilateral Controller" (S. Majima et al.), Mechatronics 1991.

"Anthropomorphic Remote Manipulator", NASA Tech Briefs 1991.

"Controlling Remote Manipulators through Kinesthetic Coupling" (A.K. Bejczy), Computers in Mechanical Engineering 1983.

"Design of a Surgeon–Machine Interface for Teleoperated Microsurgery" (Steve Charles M.D. et al.), IEEE 1989.

"A Robot in an Operating Room: A Bull in a China Shop" (J.M. Dolan et al.), IEEE 1987.

Abstract of a presentation "Concept and Experimental Application of a Surgical Robotic System the Steerable MIS Instrument SMI" given at the 3rd World Congress of Endoscopic Surgery in Bordeaux, Jun. 18–20, 1992.

Abstract of a presentation given at the 3rd World Congress of Endoscopic Surgery in Bordeaux, Jun. 18–20, 1992, entitled "Session 15/1".

Abstract of a presentation "A Pneumatic Controlled Sewing Device for Endoscopic Application the MIS Sewing Instrument MSI" given at the 3rd World Congress of Endoscopic Surgery in Bordeaux, Jun. 18–20, 1992.

Abstract of a presentation given at the 3rd World Congress of Endoscopic Surgery in Bordeaux (Jun. 18–20, 1992), entitled "Session 15/2".

Abstract of a presentation given at the 3rd World Congress of Endoscopic Surgery in Bordeaux (Jun. 18–20, 1992), entitled Session 15/4.

Abstract of a presentation given at the 3rd World Congress of Endoscopic Surgery in Bordeaux (Jun. 18–20, 1992), entitled "Session 15/5".

"Properties of Master–Slave Robots" (C. Vibet), Motor–con 1987.

"A New Microsurgical Robot System for Corneal Transplantation" (Noriyuki Tejima), Precision Machinery 1988.

"Human/Robot Interaction via the Transfer of Power and Information Signals—Part I: Dynamics and Control Analysis" (H. Kazerooni), IEEE 1989.

"Human/Robot Interaction via the Transfer of Power and Information Signals—Part II: An Experimental Analysis" (H. Kazerooni), IEEE 1989.

"Power and Impedance Scaling in Bilateral Manipulation" (J. Edward Colgate), IEEE 1991.

"S.M.O.S.: Stereotaxical Microtelemanipulator for Ocular Surgery" (Aicha Guerrouad and Pierre Vidal), IEEE 1989.

"Motion Control for a Sheep Shearing Robot" (James P. Trevelyan et al.), Proceedings of the 1st International Symposium on Robotics Research, MIT, Cambridge, Massachusetts, USA 1983.

"Robots and Telechirs" (M.W. Thring), Wiley 1983.

Industrial Robotics (Gordon M. Mair), Prentice Hall 1988 (pp. 41–43, 49–50, 54, 203–209 enclosed).

"Student Reference Manual for Electronic Instrumentation Laboratories" (Wolf et al.), Prentice Hall, New Jersey 1990, pp. 498 and 499.

"Surgery in Cyberspace" (Taubes), Discover Magazine, Dec. 1994.

* cited by examiner

INSTRUMENT GUIDE

BACKGROUND OF THE INVENTION

1. Field of the Invention

The present invention relates to an instrument guide for guiding a surgical instrument into a patient.

2. Prior Art

There have been developed various procedures to perform minimally invasive surgery. For example, there have been developed minimally invasive procedures to perform a coronary artery bypass graft (CABG). The minimally invasive CABG procedure can be performed with a robotic system sold by Computer Motion, Inc., the assignee of the present invention, under the trademark ZEUS.

The ZEUS system includes a plurality of robotic arms that can control the movement of surgical instruments inserted through small incisions in the patient. The surgical instruments move in accordance with the movement of handles held by a surgeon. The handles are located at a console that allows the surgeon to view a monitor that is coupled to an endoscope inserted into the patient. The surgeon can perform a surgical procedure by moving the handles and viewing the surgical site displayed by the monitor.

Performing a minimally invasive procedure may require a number of different surgical instruments. Each robotic arm of the ZEUS system has a coupling mechanism that allows instruments to be attached to, and detached from, the arm. The surgeon, or a surgeon assistant can readily replace instruments during a procedure.

The instruments are typically inserted through a trocar that penetrates the body cavity of the patient. The ZEUS system utilizes the incision point of the patient as a pivot point for the robotic arm and the surgical instrument. The system utilizes a software routine that transforms the coordinates of the surgical instruments to stationary world coordinates to provide commands that accurately move the instruments.

An instrument guide may be placed within the trocar to guide the instrument, maintain robotic arm positioning and facilitate instrument exchanges during surgery. The inner diameter of the instrument guide has approximately the same diameter as the outer diameter of the surgical instrument to prevent relative radial movement between the instrument and the guide. Any excessive space between the surgical instrument and the instrument guide may result in a lag between the movement of the handles and the movement of the instrument. This lag may increase the complexity of performing the procedure.

The outer diameter of the surgical instruments may vary from instrument to instrument. Smaller surgical instruments may create an undesired space between the instrument and the guide. It would be desirable to provide an instrument guide that can be secured to a variety of surgical instruments each having a different outer diameter.

BRIEF SUMMARY OF THE INVENTION

One embodiment of the present invention is an instrument guide that can be inserted into a patient and guide a surgical instrument. The instrument guide includes a shaft that has an inner channel adapted to receive the surgical instrument. The guide also has a leaf that extends from the shaft. The leaf is adapted to move relative to the shaft when the surgical instrument is inserted into the inner channel.

DETAILED DESCRIPTION OF THE PREFERRED EMBODIMENT

In general the present invention includes an instrument guide that can compensate for surgical instruments that have different outer diameters. The instrument guide includes a shaft that has an inner channel adapted to receive a surgical instrument. The guide also has a leaf that can be deflected relative to the shaft to exert a spring force onto the instrument. The amount of leaf deflection is dependent upon the outer diameter of the surgical instrument.

Figure 1:
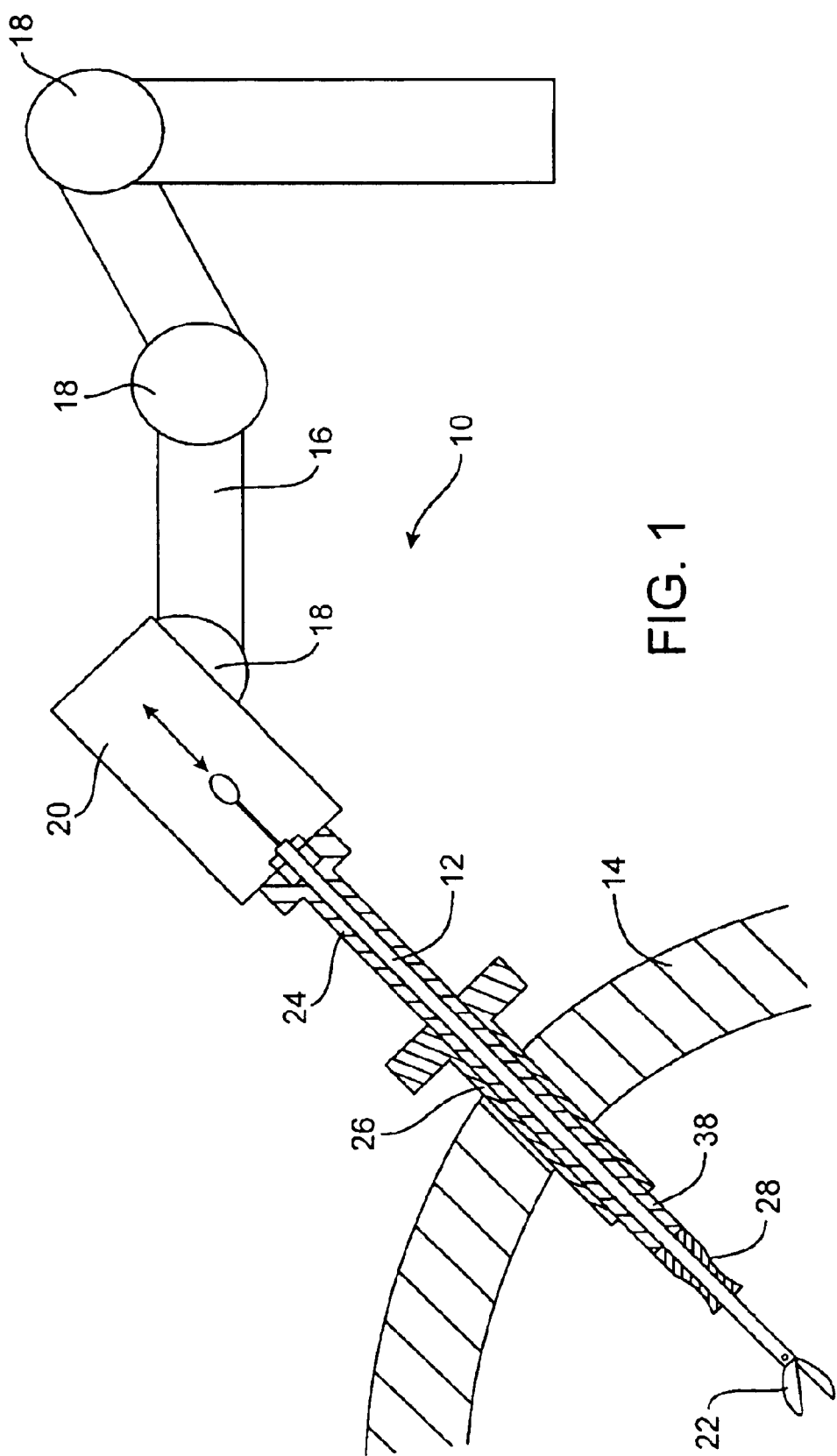
FIG. 1 is an illustration of an embodiment of a robotic surgical system of the present invention.

Referring to the drawings more particularly by reference numbers, FIG. 1 shows an embodiment of a robotic surgical system 10 of the present invention. The system 10 may include a surgical instrument 12 that extends through a body cavity 14 of a patient. The instrument 12 may be coupled to a robotic arm 16. The robotic arm 16 may include a number of active joints 18 that can be activated to move the instrument 12 relative to the patient. The arm 16 may also have one or more passive joints (not shown) that allow the instrument 12 to pivot about the incision point of the patient.

The surgical instrument 12 may be connected to a tool driver 20 that can both spin the instrument 12 and actuate an instrument end effector 22. The tool driver 20 can be configured to allow an operator to readily connect and disconnect the instrument 12 from the driver 20.

The robotic arm 16 and tool driver 20 can be actuated in accordance with the manipulation of handles (not shown) by the surgeon. Such a system may be the same or similar to a robotic system sold by Computer Motion, Inc. under the trademark ZEUS and disclosed in U.S. Pat. No. 6,007,550 issued to Wang et al., which are hereby incorporated by reference.

The surgical instrument 12 may extend through an instrument guide 24. The instrument guide 24 may extend through a port element such as a trocar 26 that is inserted into the patient. The instrument guide 24 can be used to guide the instrument 12 through the trocar 26. Although a trocar is shown and described, it is to be understood that the instrument guide 24 can be inserted through a cannula or other port element.

Figure 2:
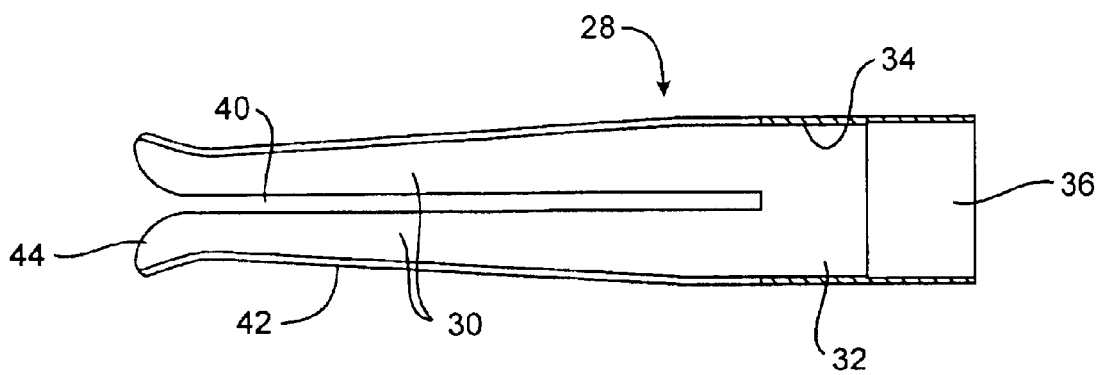
FIG. 2 is a side view of an instrument guide tip of the robotic surgical system.

Referring to FIG. 2, the instrument guide 24 may include a guide tip 28 which has a plurality of leaves 30 that extend from a shaft 32. By way of example, the guide tip 28 may have a plurality of leaves 30. The shaft 32 may have an inner channel 34 that is adapted to receive the surgical instrument 12. A proximal end of the tip 28 may have a bore 36 that can be pressed into an end of a tube 38 portion of the guide 24 that extends through the trocar 26 as shown in FIG. 1. The guide tube 38 may be attached to the tool driver 20.

Referring again to FIG. 2, the leaves 30 are separated by slots 40. The slots 40 allow the leaves 30 to be deflected in an outward direction when the instrument 12 is inserted through the inner channel 34. The amount of deflection is dependent upon the outer diameter of the surgical instrument 12. The leaves 30 exert a spring force onto the surgical instrument 12 to prevent radial movement between the instrument 12 and the guide 24. The deflecting leaves 30 compensate for various instrument outer diameters while securing the instrument at the pivot point of the system. Each leaf 30 may have an inner tapered portion 42 and a lip 44 configured to reduce the difficulty of retracting the instrument 12 from the guide 24.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those ordinarily skilled in the art.

Figure 3:
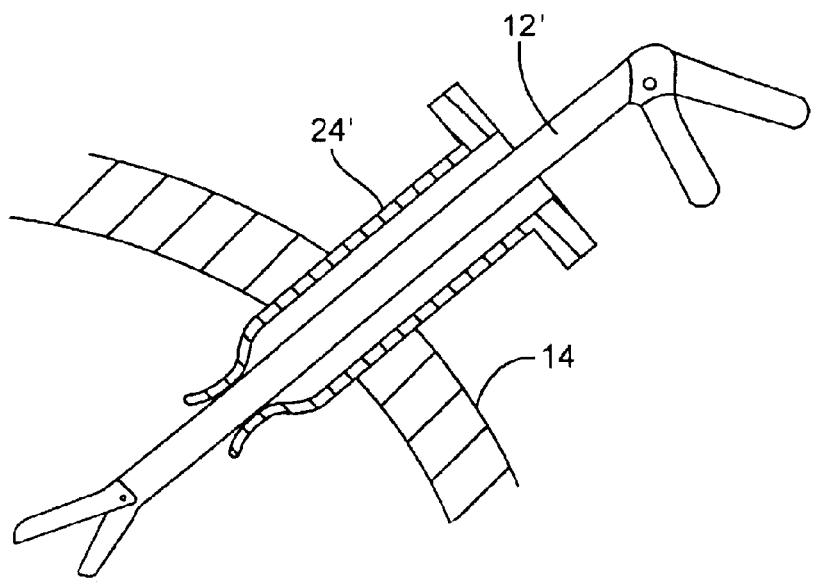
FIG. 3 is an illustration of the instrument guide used with a manually actuated surgical instrument.

For example, although the instrument guide 24 is shown inserted into a trocar and attached to a robotic arm, as shown in FIG. 3 the guide 24' can be inserted into the body cavity 14 without a trocar. Additionally, the surgical instrument 12' may be a manually actuated device that is not attached to a robotic arm. In this embodiment the instrument guide 24' is configured as a trocar that can be inserted into a patent.

What is claimed is:

1. An instrument guide that can be inserted into a patient and guide a surgical instrument that has a diameter, comprising:
   a shaft that has an inner channel; and,
   a plurality of leaves that extend from said shaft, said leaves being separated by a space having an inner diameter that is smaller than the diameter of the surgical instrument so that said leaves move when the surgical instrument is inserted into the inner channel, each leaf has a tapered portion and a lip.

2. The instrument guide of claim 1, wherein said leaves are separated by a plurality of slots.

3. The instrument guide of claim 1, wherein said leaves exert a spring force on the surgical instrument.

4. An instrument guide assembly that can be inserted into a patient and support a surgical instrument that has a diameter, comprising:
   a port element that has an inner channel; and
   an instrument guide that can be inserted into said inner channel of said port element, said instrument guide having a shaft that has an inner channel, and a plurality of leaves that extend from said shaft, said leaves being separated by a space having an inner diameter that is smaller than the diameter of the surgical instrument so that said leaves move relative to said shaft when the surgical instrument is, inserted into the inner channel, each leaf has a tapered portion and a lip.

5. The assembly of claim 4, wherein said leaves are separated by a plurality of slots.

6. The assembly of claim 4, wherein said leaves exert a spring force on the surgical instrument.

7. The assembly of claim 4, wherein said port element is a trocar.

8. The assembly of claim 4, wherein said port element is a cannula.

9. A trocar that can guide a surgical instrument that has a diameter, comprising:
   a shaft that has an inner channel and,
   a plurality of leaves that extend from said shaft, said leaves being separated by a space having an inner diameter that is smaller than the diameter of the surgical instrument so that said leaves move relative to said shaft when the surgical instrument is inserted into the inner channel, each leaf has a tapered portion and a lip.

10. The trocar of claim 9, wherein said-leaves are separated by a plurality of slots.

* * * * *